United States Patent
Bucher et al.

(10) Patent No.: US 7,367,688 B1
(45) Date of Patent: May 6, 2008

(54) OUTDOOR LIGHTING LAMP WITH WATER-RESISTANT COVER

(75) Inventors: John C. Bucher, Hillsboro Beach, FL (US); Charles W. Geyer, Atlanta, GA (US)

(73) Assignee: King of Fans, Inc., Ft. Lauderdale, FL (US)

( * ) Notice: Subject to any disclaimer, the term of this patent is extended or adjusted under 35 U.S.C. 154(b) by 42 days.

(21) Appl. No.: 11/544,986

(22) Filed: Oct. 6, 2006

(51) Int. Cl.
*F21V 29/00* (2006.01)

(52) U.S. Cl. .................. 362/267; 362/145; 362/264; 362/294; 362/373

(58) Field of Classification Search ............... 362/267, 362/145, 147, 645, 546, 547, 548, 549, 518, 362/220, 221, 224, 225, 264, 265, 294, 373; 29/700
See application file for complete search history.

(56) References Cited

U.S. PATENT DOCUMENTS

| | | | | |
|---|---|---|---|---|
| 3,082,320 A * | 3/1963 | Cook | ................... | 362/310 |
| 3,588,488 A * | 6/1971 | Lauterbach | ................ | 362/2 |
| 3,754,133 A * | 8/1973 | Youdin et al. | ............ | 362/267 |
| 5,971,573 A | 10/1999 | Bucher et al. | ............ | 362/435 |
| 6,174,077 B1 | 1/2001 | Bucher et al. | ............ | 362/435 |
| 6,183,117 B1 | 2/2001 | Bucher et al. | ............ | 362/438 |
| 6,193,397 B1 | 2/2001 | Bucher et al. | ............ | 362/438 |
| 6,200,008 B1 | 3/2001 | Bucher et al. | ............ | 362/438 |
| 6,224,226 B1 | 5/2001 | Bucher et al. | ............ | 362/96 |
| 6,392,541 B1 | 5/2002 | Bucher et al. | ............ | 340/541 |
| 6,536,926 B2 | 3/2003 | Bucher et al. | ............ | 362/438 |
| 6,776,508 B2 | 8/2004 | Bucher et al. | ............ | 362/293 |
| 6,926,423 B2 | 8/2005 | Bucher et al. | ............ | 362/184 |

* cited by examiner

*Primary Examiner*—Jacob Y. Choi
(74) *Attorney, Agent, or Firm*—Brian S. Steinberger; Law Offices of Brian S. Steinberger, P.A.

(57) ABSTRACT

Lamp devices, apparatus, methods of use, and methods of assembly which can be used with a single suspension lamp and/or with a plurality of suspension lamps. Each lamp can have a lamp seat mounted on a tubular member that is fixed to a main body. The lamp seat can be connected electrically to a circuit unit housed in the main body, and is mounted with a lamp bulb. A bowl-shaped upper lamp shade surrounds the lamp seat, is mounted on the tubular member, and is formed with heat-dissipating holes. A lower lamp shade is coupled detachably to a larger-diameter lower open end of the upper lamp shade, and cooperates with the upper lamp shade to define an accommodating space for receiving an assembly of the lamp seat and the lamp bulb. A bowl-shaped water-resistant cover is mounted on the tubular member, and is disposed above the upper lamp shade for covering the upper lamp shade.

9 Claims, 4 Drawing Sheets

OUTDOOR LIGHTING LAMP WITH WATER-RESISTANT COVER

This invention relates to lights, in particular to outdoor lamp devices, apparatus, and methods of assembly and use that can be used with or without overhead fans that restrict condensation and water from entering into the lamps.

BACKGROUND AND PRIOR ART

Traditional electrically powered lights such as those shown and described in reference to FIG. 1 have been known to become damaged from water from condensation formed from different temperature conditions and humidity when being used in non-air-conditioned environments such as on porches and the like. This condensation problem is a long term problem especially in southern warm and humid climates such as Florida and the southern United States. These lights while not intended for outdoor use still have the condensation problem when used in non-air-conditioned spaces such as under overhangs and in porches, decks and the like.

The general components of a known indoor type electrically powered suspension type lamp is shown in FIG. 1. This lamp has been found to allow for water to easily enter into the light causing damage. The lamp shown in FIG. 1 is generally used for indoor use.

Referring to FIG. 1, a conventional indoor suspension lamp can include a connecting member 6, a lamp seat 1 mounted on a lower end of the connecting member 6, a spiral compact lamp bulb 2 mounted on the lamp seat 1, a bowl-shaped upper lamp shade 3 surrounding the lamp seat 1 and having a smaller-diameter upper open end mounted on the connecting member 6, and a larger-diameter lower open end, and a lower lamp shade 4 having an upper open end coupled detachably to the larger-diameter lower open end of the upper lamp shade 3 and cooperating with the upper lamp shade 3 to define an accommodating space 7 for receiving an assembly of the lamp seat 1 and the lamp bulb 2.

In order to dissipate heat generated by the lamp bulb 2, the upper lamp shade 3 needs to include a plurality of heat-dissipating holes 5 that pass completely through the shade 3 from one side to the other, and which can inherently cause other problems.

Water has been found to leak into the accommodating space 7 via the heat-dissipating holes 5 in these conventional type lamps. The water can be the result of condensation formed from temperature differentials, and/or if used outdoors, then additionally from rain storms, and the like. The water entering into the lamp can and has been found to easily damage the lamp seat 1, thereby result in dangerous short circuits, during use. Such short circuits can be further dangerous to persons needing the lamp to be in operation during storm conditions such as during rainstorms, and hurricanes where visibility is required.

Additionally, the lifespan of using the conventional indoor suspension lamp in outdoor environments would also be severely limited since it would not work over long periods of time.

Sealing the conventional indoor suspension lamp against water leakage would not work since the heat must be dissipated and any sealing of the lamp body can result in other damage such as overheating, fire, and the like.

Using elaborate known outdoor lamps may not be practical and can be cost prohibitive since their manufacturing and assembly costs would be substantially more than the indoor conventional suspension lamp.

Thus, the need exists for solutions to the above problems with the prior art.

SUMMARY OF THE INVENTION

A primary objective of the present invention is to provide an electrically powered indoor suspension lamp device, apparatus, method of assembly and use, that can be used in environments where condensation forms and/or outdoors, where water is eliminated from entering into and damaging electrical components in the lamp housing.

A secondary objective of the present invention is to provide an electrically powered indoor suspension lamp device, apparatus, method of assembly and use, that can be easily interchangeably used both indoors and outdoors as a lamp.

A third objective of the present invention is to provide an electrically powered indoor suspension lamp device, apparatus, method of assembly and use, that can be used both indoors and outdoors with or without a ceiling fan.

A fourth objective of the present invention is to provide an electrically powered indoor suspension lamp device, apparatus, method of assembly and use, that can be retrofitted and converted to use in environments where condensation forms and/or for outdoor use.

A fifth objective of the present invention is to provide a conventional electrically powered indoor suspension lamp device, apparatus, method of assembly and use, that can be easily and inexpensively adapted for environments where condensation forms, and/or for outdoor use.

A sixth objective of the present invention is to provide an electrically powered indoor suspension lamp device, apparatus, method of assembly and use, that can be used both indoors and outdoors as a lamp, and has substantially greater longevity over conventional suspension lamp devices.

A seventh objective of the present invention is to provide an electrically powered indoor suspension lamp device, apparatus, method of assembly and use, that can be used both indoors and outdoors as a lamp which allows for adequate and safe heat dissipation from the lamp while maintaining a waterproof seal for the lamp components.

A seventh objective of the present invention is to provide an electrically powered outdoor suspension lamp device, apparatus, method of assembly and use, that is less expensive than most outdoor lamps.

In a preferred embodiment, the invention can include a main body adapted to be attached to a surface, a circuit unit housed in the main body, and a suspension lamp unit, with a lamp shade and a novel bowl-shaped water-resistant cover.

The lamp unit can include a tubular member having an upper end portion connected fixedly to the main body, and a lower end portion, a lamp seat mounted on the lower end portion of the tubular member and connected electrically to the circuit unit, a lamp bulb mounted on the lamp seat, a bowl-shaped upper lamp shade surrounding the lamp seat and having a smaller-diameter upper open end mounted on the tubular member, and a larger-diameter lower open end having a diameter larger than that of the upper open end of the upper lamp shade, the upper lamp shade being formed with a plurality of heat-dissipating holes.

The lamp shade can have an upper open end coupled detachably to the larger-diameter lower open end of the upper lamp shade and cooperating with the upper lamp shade to define an accommodating space for receiving an assembly of the lamp seat and the lamp bulb.

The bowl-shaped water-resistant cover can have an upper open end that is mounted on the tubular member and that is disposed above and that has a diameter larger than that of the upper open end of the lamp shade, and a lower open end that has a diameter larger than that of the lower open end of the lamp shade and that is disposed on the upper open end of the lower lamp shade so as to cover the lamp shade.

A method of converting an indoor suspension lamp to prevent water intrusion into the lamp, can include the steps of providing a lamp having a dome shaped shade that covers an electrical light source, and having through-holes for allowing heat dissipation from the light source, attaching a dome shaped cover having a solid contiguous surface over the dome shaped shade so that as to form a space therebetween surrounding the shade, and preventing water from directly passing through the heat dissipation through-holes by the cover.

The dome shaped cover can include a bottom lip edge having a smaller diameter than a lower outer edge of the dome shaped cover.

The providing step can include the step of attaching the lamp to a ceiling based mount. Alternatively, the providing step can include the step of providing a ceiling fan above the lamp.

The step of attaching the dome shaped cover can include the step of mounting the dome shaped cover to a tubular member from which the lamp is suspended.

The mounting step can include the steps of providing the dome shaped cover with a through-hole in a top portion of the cover, providing the dome shaped shade with a through-hole in a top portion of the shade, and mounting the dome shaped cover and the dome shaped shade by their respective top portion through-holes with the tubular member passing therethrough.

The method can include the step of dissipating heat from the lamp source through the heat-dissipating through holes in the shade into a larger space that is formed by the space between the shade and the cover so that the heat fills into the larger space.

The method can include the step of dissipating heat from the lamp source through the heat-dissipating through holes in the shade so that the dome shaped cover functions as heat exchanger with ambient air.

The method can further include the steps of providing a second lamp having a second dome shaped shade that covers a second electrical light source, and having through-holes for allowing heat dissipation from the light source, attaching a second dome shaped cover having a solid contiguous surface over the second dome shaped shade so that as to form a space therebetween surrounding the second shade, and preventing the water from directly passing through the heat dissipation through-holes by the second cover.

The invention can be used with a single suspended lamp. The invention can also be used with a plurality of suspended lamps The invention can be used with stand alone lamps that are suspended from a ceiling mount with or without a ceiling fan. The invention can be used with wall or floor mounted lamps with or without ceiling fans.

Additionally, the invention can be used on a free-standing floor based pedestal stand, or table top stand having a suspension arm.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Figure 2:
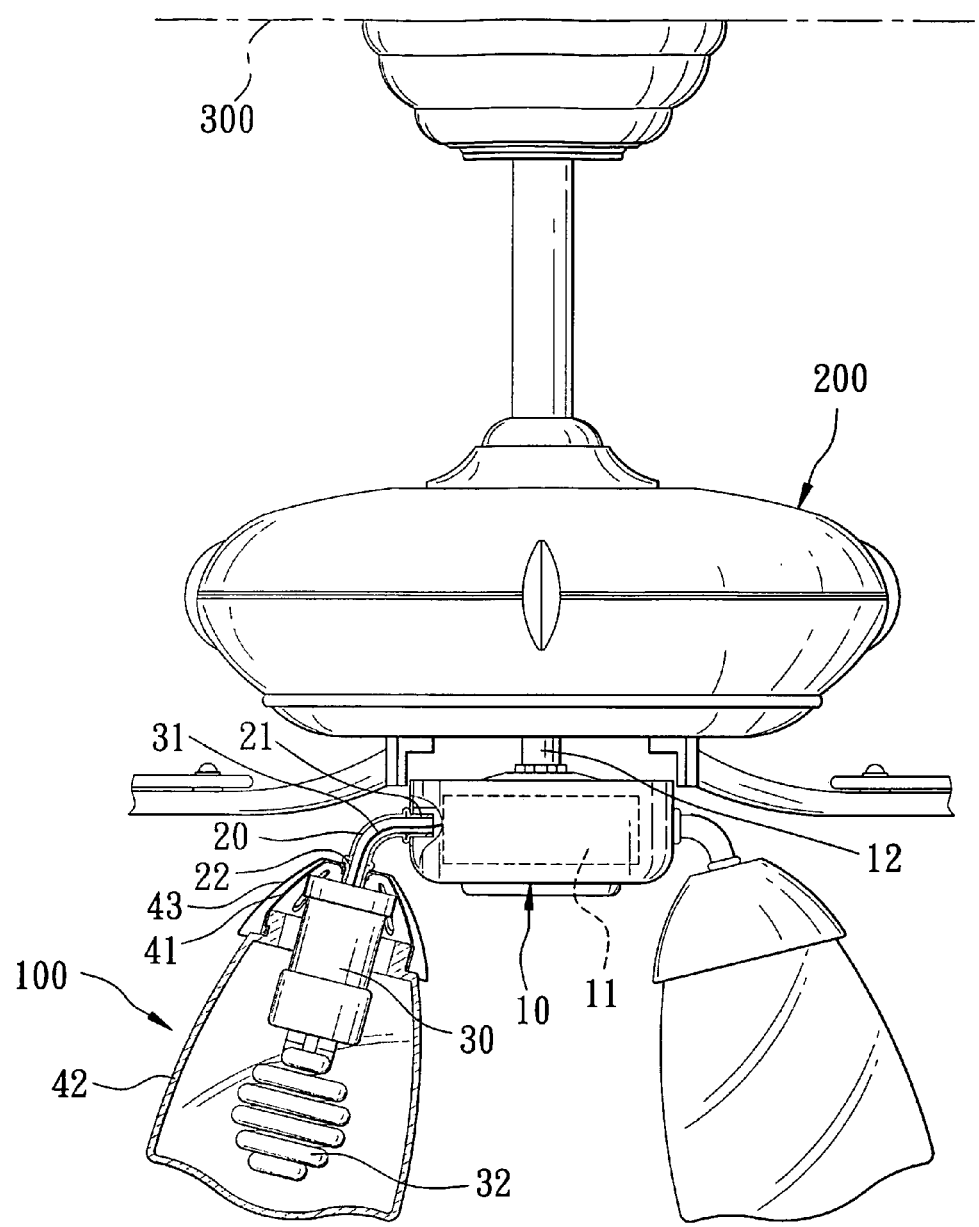
FIG. 2 illustrates a fragmentary, partly cross-sectional schematic view showing the preferred embodiment of a lamp device according to the present invention.

Referring to FIG. 2, the preferred embodiment of a lamp device according to the present invention is shown to be adapted for use with a ceiling fan 200. The lamp device can include a main body 10, an electrical circuit unit 11, and a plurality of suspension lamp units 100.

In this embodiment, the main body 10 can be disposed below the ceiling fan 200, and can be connected to the ceiling fan 200 by means of a coupling rod 12. An assembly of the main body 10 and the ceiling fan 200 can be adapted to be attached to a surface 300, such as a ceiling, overhang beam, structure, and the like. The electrical circuit unit 11 can be housed in the main body 10.

Figure 3:
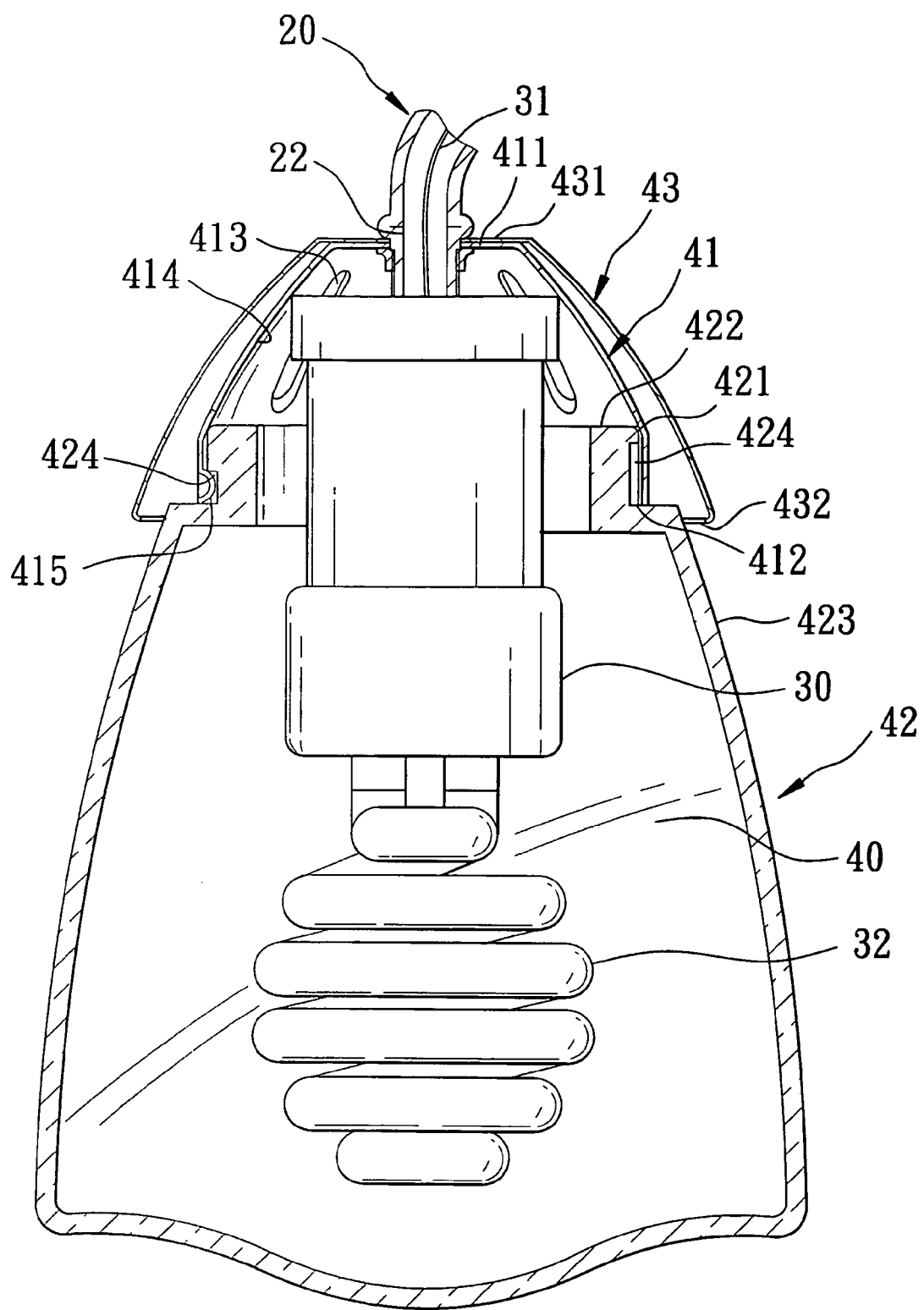
FIG. 3 illustrates a cross-sectional view showing a suspension lamp unit of the preferred embodiment.
Figure 4:
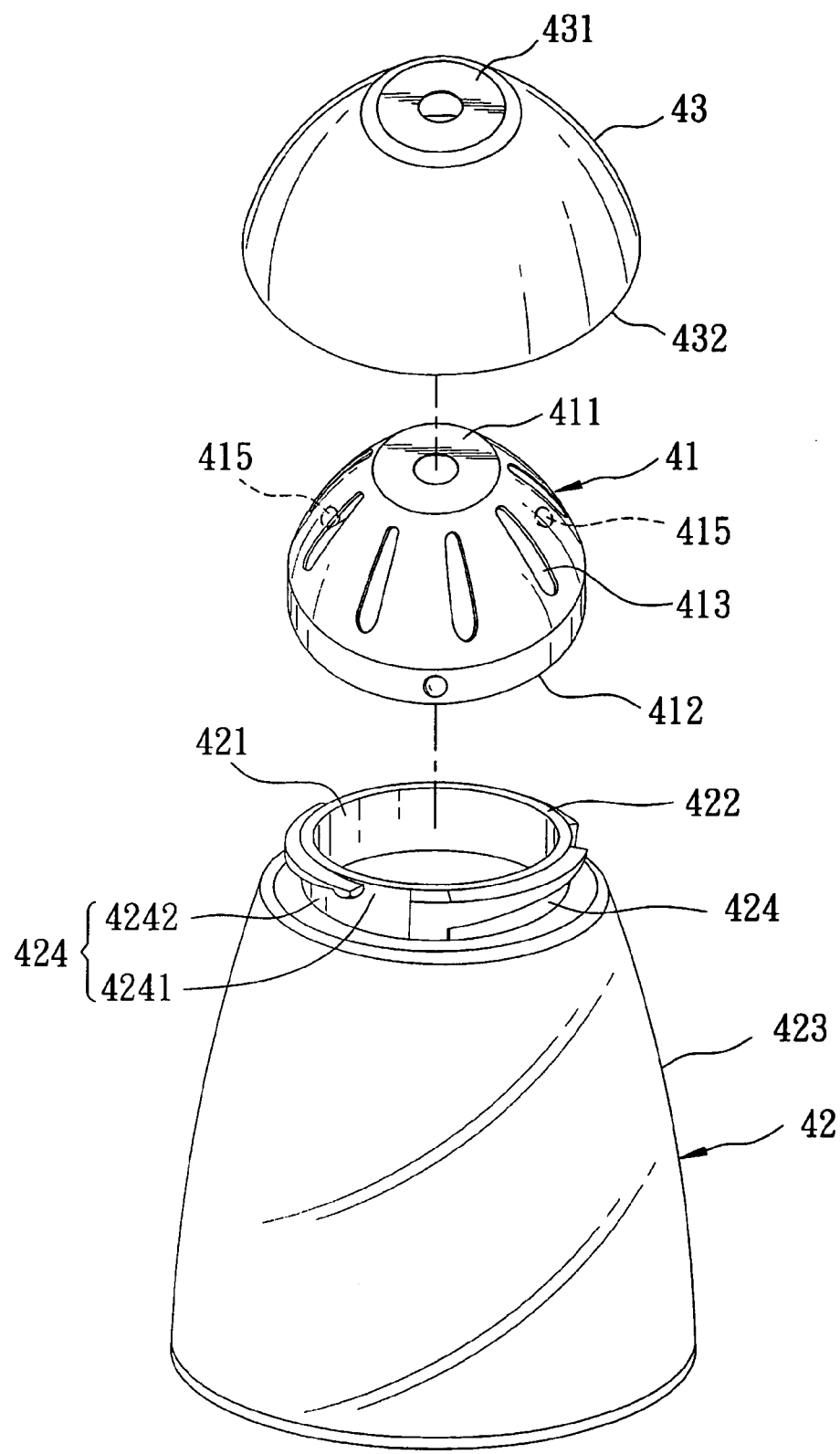
FIG. 4 shows an exploded perspective view showing a water-resistant cover, an upper lamp shade and a lower lamp shade of the suspension lamp unit of FIG. 3.

Referring further to FIGS. 3 and 4, each suspension lamp unit 100 can include a tubular member 20, a lamp seat 30, a spiral compact lamp bulb 32, a bowl-shaped upper lamp shade 41, a lower lamp shade 42, and a bowl-shaped water-resistant cover 43. The cover can be formed from molded plastic, and the like.

The tubular member 20 of each suspension lamp unit 100 can have an upper end portion 21 connected fixedly to the main body 10, and a lower end portion 22.

In each suspension lamp unit 100, the lamp seat 30 can be mounted on the lower end portion 22 of the tubular member 20, and can be connected electrically to the circuit unit 11 by a wire 31. A lamp bulb 32 can be mounted on the lamp seat 30.

For each suspension lamp unit 100, the upper lamp shade 41 can surround the lamp seat 30, and can have a smaller-diameter upper open end 411 mounted on the lower end portion 22 of the tubular member 2, and a larger-diameter lower open end 412 having a diameter larger than that of the upper open end 411. The upper lamp shade 41 can be formed with a plurality of heat-dissipating holes 413. In this embodiment, the upper lamp shade 41 can have an inner surface 414 formed with a plurality of positioning protrusions 415 that are spaced apart from each other along a circumferential direction of the lower end portion 22 of the tubular member 20 and that are disposed adjacent to the lower open end 412 of the upper lamp shade 41, as shown in FIG. 4.

The lower lamp shade 42 can have an upper open end 421 coupled detachably to the larger-diameter lower open end 412 of the upper lamp shade 41 and be cooperating with the upper lamp shade 41 to define an accommodating space 40 for receiving an assembly of the lamp seat 30 and the lamp bulb 32. In this embodiment, the lower lamp shade 42 can have a top surface 422, and an annular outer surface 423 formed with a plurality of generally L-shaped positioning grooves 424 (see FIG. 4), each of which can have a first groove portion 4241 extending downwardly from the top surface 422 for permitting passage of a corresponding one of the positioning protrusions 415 of the upper lamp shade 41 therethrough. The lower lamp shade 42 can have a curved second groove portion 4242 having an end connected to a lower end of the first groove portion 4241 and engaging the corresponding one of the positioning protrusions 415 of the upper lamp shade 41, as shown in FIG. 3.

The novel water-resistant cover 43 can have an upper open end 431 that is sleeved on the lower end portion 22 of the tubular member 20 and that is disposed above and that can have a diameter larger than that of the upper open end 411 of the upper lamp shade 41, and a lower open end 432 having a diameter larger than that of the lower open end 412 of the upper lamp shade 41. The novel cover can be disposed on the upper open end 421 of the lower lamp shade 42 so as to cover the upper lamp shade 41.

The lower open end 432 of the cover 43 can have an inwardly facing horizontal lip edge which can abut against and form a waterproof seal with the annular outer surface 423 of the lower lamp shade 42.

Additional sealing material such as gasket type materials and the like, can be used where the lip edge meets the outer surface 423 of the lamp shade 42. Additional sealing can also be provided by using additional gasket or sealing type material where upper open end 431 of water-resistant cover 43 meets lower end portion 22 of suspension lamp unit 100 as shown in FIG. 3.

The lip edge can sealingly close off the bottom of the cover 43. The lip edge at opening 432 can additionally have through-holes for allowing any water drainage out the bottom. Alternatively, the lip edge at 432 can be spider shaped with spaces for allowing any excess water to drain out therefrom.

The air space between upper lamp shade 41 and the outer cover 43 can have an annular type shaped space which allows heat that is generated from lamp source 32 to pass into the space. The combination of this encircling air space and the large surface area of cover 43 can further function as a heat exchanger to pass the heat from light source 32 to the ambient air outside of the cover 43.

As previously described, the cover 43 can be formed from molded plastic. Additionally, the cover 43 can be formed from metal. Forming the outer cover out of metal such as aluminum or galvanized metal can further create a heat sink effect that can further absorb and dissipate the heat generated from the lamp source 32.

With the presence of the water-resistant cover 43 for covering the upper lamp shade 41, the water leakage problem encountered in the prior art can be avoided when employing the lamp device in environments where condensation can form as well as for most outdoor use.

The invention can be used with a newly manufactured single lamp. The invention can be used with a plurality of newly manufactured lamps. The invention can be retrofitted with an existing suspended lamp. The invention can be retrofitted into a plurality of suspended lamps.

The novel water-resistant cover does not substantially alter the appearance of the lamp since the dome shaped cover is similar in appearance to the dome shaped shade.

The novel invention can be manufactured and assembled with suspension lamps that are ceiling mounted, and the like, with or without ceiling fans. The invention can also be used with wall or floor mounted lamps or floor stands with or without fans.

Additionally, the invention can be used on a free-standing floor based pedestal stand, or table top stand having a suspension arm.

Figure 1:
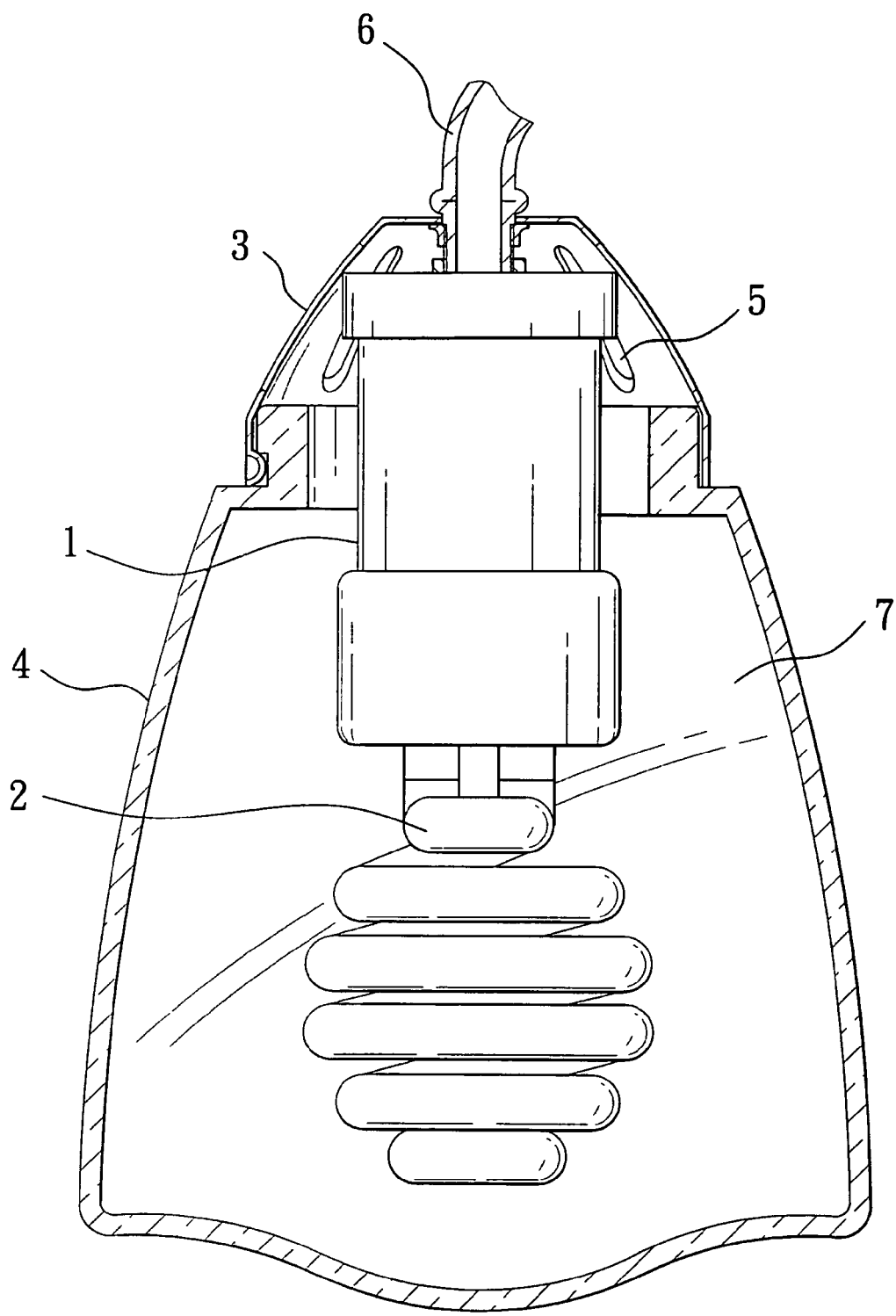
FIG. 1 illustrates a cross-sectional view of a conventional suspension lamp unit.

Still furthermore, the invention can be used as a retrofit for modifying the indoor suspension lamps of FIG. 1 into a water-resistant application for outdoor use and/or for use in humid and wet environments.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A lamp assembly comprising: a main body adapted for attaching to a surface;
   a circuit unit housed in said main body; and
   a suspension lamp unit including
   a tubular member having an upper end portion connected fixedly to said main body, and a lower end portion,
   a lamp seat mounted on said lower end portion of said tubular member and connected electrically to said circuit unit,
   a lamp bulb mounted on said lamp seat,
   a bowl-shaped upper lamp shade surrounding said lamp seat and having a smaller-diameter upper open end mounted on said tubular member, and a larger-diameter lower open end having a diameter larger than that of said upper open end of said upper lamp shade, said upper lamp shade being formed with heat-dissipating holes,
   a lower lamp shade having an upper open end coupled detachably to said larger-diameter lower open end of said upper lamp shade and cooperating with said upper lamp shade to define an accommodating space for receiving an assembly of said lamp seat and said lamp bulb, and
   a bowl-shaped water-resistant cover having an upper open end that is mounted on said tubular member and that is disposed above has a diameter larger than that of said upper open end of said upper lamp shade, and a lower open end that has a diameter larger than that of said lower open end of said upper lamp shade and that is disposed on said upper open end of said lower lamp shade so as to cover said upper lamp shade, wherein the water-resistant cover stops water from directly passing into the heat dissipating holes.

2. The lamp assembly of claim 1, wherein said upper lamp shade includes:
   an inner surface formed with a plurality of positioning protrusions spaced apart from each other along a circumferential direction of said lower end portion of said tubular member, that are disposed adjacent to said lower open end of said upper lamp shade;
   and said lower lamp shade includes:
   a top surface, and annular outer surface formed with a plurality of generally L-shaped positioning grooves, each of which has a first groove portion extending downwardly from said top surface for permitting passage of a corresponding one of said positioning protrusions of said upper lamp shade therethrough, and a curved second groove portion having an end connected to a lower end of said first groove portion and engaging the corresponding one of said positioning protrusions of said upper lamp shade.

3. The lamp assembly of claim 1, wherein the main body includes:
a ceiling mount.

4. The lamp assembly of claim 1, wherein the main body includes:
a ceiling fan.

5. The lamp assembly of claim 1, wherein the bow shaped water-resistant cover includes:
an inwardly facing bottom lip edge having a smaller diameter than a lower outer edge of the dome shaped cover, the bottom lip edge for abutting against the shade.

6. The lamp assembly of claim 5, wherein the bottom lip edge includes:
a drainage hole for allowing water to drain out therefrom.

7. A plurality of suspended lamps having water resistant covers, comprising:
a plurality of suspension lamp units, each lamp unit including
a tubular member having an upper end portion connected fixedly to said main body, and a lower end portion,
a lamp seat mounted on said lower end portion of said tubular member and connected electrically to a circuit unit,
a lamp bulb mounted on said lamp seat,
a bowl-shaped upper lamp shade surrounding said lamp seat and having a smaller-diameter upper open end mounted on said tubular member, and a larger-diameter lower open end having a diameter larger than that of said upper open end of said upper lamp shade, said upper lamp shade being formed with heat-dissipating holes,
a lower lamp shade having an upper open end coupled detachably to said larger-diameter lower open end of said upper lamp shade and cooperating with said upper lamp shade to define an accommodating space for receiving an assembly of said lamp seat and said lamp bulb, and
a bowl-shaped water-resistant cover having an upper open end that is mounted on said tubular member and that is disposed above has a diameter larger than that of said upper open end of said upper lamp shade, and a lower open end that has a diameter larger than that of said lower open end of said upper lamp shade and that is disposed on said upper open end of said lower lamp shade so as to cover said upper lamp shade, wherein the water-resistant cover stops water from directly passing into the heat dissipating holes, and wherein the plurality of suspended lamps are suspended from a single member.

8. The plurality of suspended lamps of claim 7, wherein the single member is a ceiling mount.

9. The plurality of suspended lamps of claim 7, wherein the single member is a ceiling fan.

* * * * *